United States Patent
Webb et al.

(10) Patent No.: US 12,226,317 B2
(45) Date of Patent: *Feb. 18, 2025

(54) METAL-BACKED TIBIAL COMPONENT OF AN ORTHOPAEDIC KNEE PROSTHESIS AND ASSOCIATED METHOD OF MAKING THE SAME

(71) Applicant: DEPUY IRELAND UNLIMITED COMPANY, Ringaskiddy (IE)

(72) Inventors: Anthony J. Webb, Fort Wayne, IN (US); Nicholas A. Miltner, Fort Wayne, IN (US); Evan P. O'Mahony, Cork (IE); Fionnan A. Mcnamara, Rathvilly (IE); Edward P. Kavanagh, Mallow (IE); Dustin N. Albert, Warsaw, IN (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 959 days.

This patent is subject to a terminal disclaimer.

(21) Appl. No.: 17/240,185

(22) Filed: Apr. 26, 2021

(65) Prior Publication Data

US 2021/0244545 A1 Aug. 12, 2021

Related U.S. Application Data

(63) Continuation-in-part of application No. 16/717,077, filed on Dec. 17, 2019, now Pat. No. 11,357,635.

(51) Int. Cl.
*A61F 2/38* (2006.01)
*A61F 2/30* (2006.01)

(52) U.S. Cl.
CPC ..... *A61F 2/389* (2013.01); *A61F 2002/30011* (2013.01); *A61F 2002/3006* (2013.01)

(58) Field of Classification Search
CPC ............ A61F 2/3877; A61F 2/3094; A61F 2002/30125; A61F 2002/30892; A61F 2002/30973; A61F 2002/30985; A61F 2310/00029; A61F 2002/30891; A61F 2002/30878; A61F 2002/30011; A61F 2002/3093

See application file for complete search history.

(56) References Cited

U.S. PATENT DOCUMENTS

| | | | |
|---|---|---|---|
| 4,479,271 | A | 10/1984 | Bolesky et al. |
| 4,997,445 | A | 3/1991 | Hodorek |
| 5,019,104 | A | 5/1991 | Whiteside et al. |
| 5,702,465 | A | 12/1997 | Burkinshaw |
| 6,682,567 | B1 | 1/2004 | Schroeder |
| 7,578,851 | B2 | 8/2009 | Dong et al. |

(Continued)

FOREIGN PATENT DOCUMENTS

| | | |
|---|---|---|
| AU | 2010237755 A1 | 5/2011 |
| JP | 2014503267 A | 2/2014 |

OTHER PUBLICATIONS

English translation of Japanese Office Action for Japanese Application No. 2022-537058, Aug. 21, 2024, 7 pages.

*Primary Examiner* — Brian A Dukert
*Assistant Examiner* — Melissa A Hoban
(74) *Attorney, Agent, or Firm* — Barnes & Thornburg LLP

(57) ABSTRACT

An orthopaedic implant includes a tibial component having a metal base with a polymer bearing molded thereto. A method for making a tibial component is also disclosed.

16 Claims, 12 Drawing Sheets

(56) References Cited

U.S. PATENT DOCUMENTS

| | | |
|---|---|---|
| 8,864,826 B2 | 10/2014 | Pressacco |
| 2004/0034432 A1 | 2/2004 | Hughes et al. |
| 2012/0197264 A1 | 7/2012 | Todd et al. |
| 2012/0209393 A1 | 8/2012 | Ries et al. |
| 2012/0323335 A1 | 12/2012 | Parisi et al. |
| 2013/0110248 A1 | 5/2013 | Zipnick |
| 2013/0166035 A1 | 6/2013 | Landon |
| 2014/0142714 A1* | 5/2014 | Wright .................. A61F 2/389 623/20.31 |
| 2018/0064543 A1 | 3/2018 | Wright et al. |
| 2019/0125541 A1 | 5/2019 | Axelson et al. |
| 2019/0290441 A1 | 9/2019 | Tong et al. |

* cited by examiner

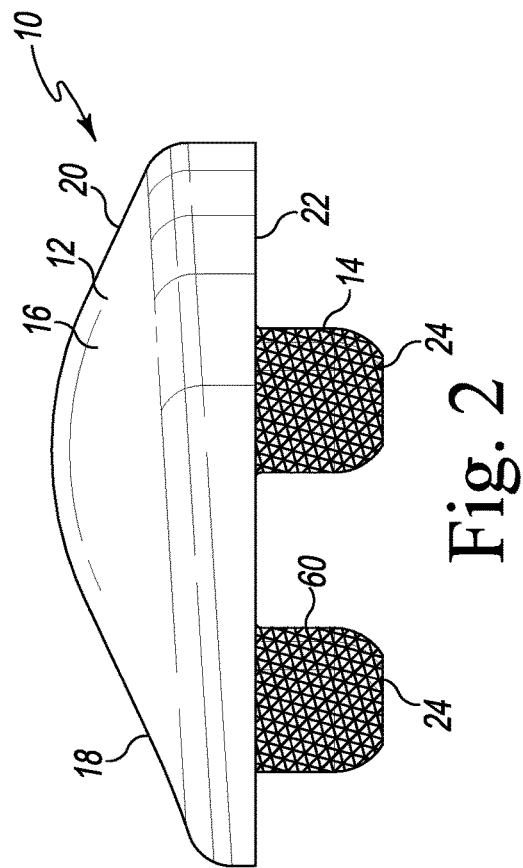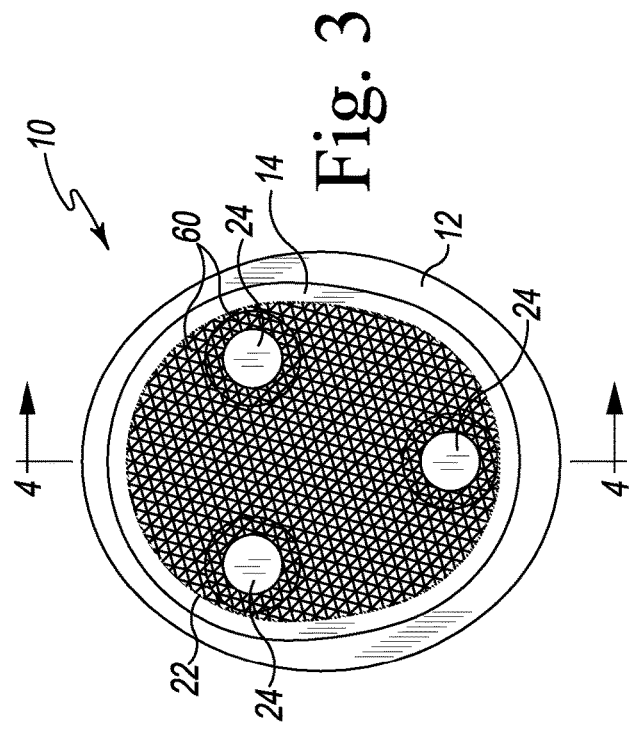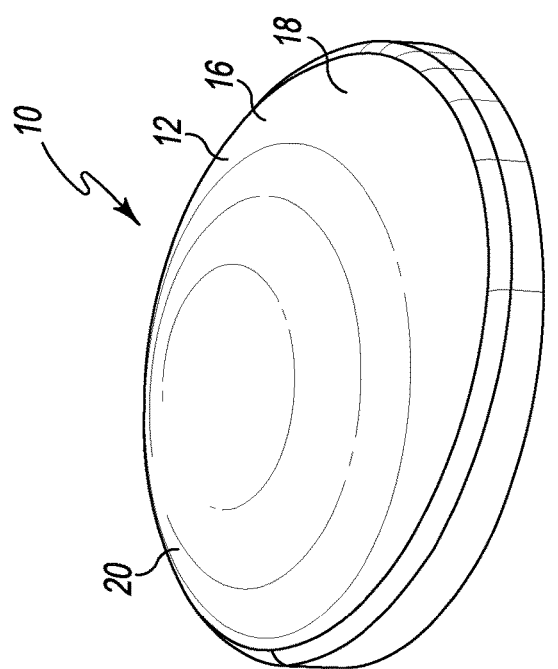

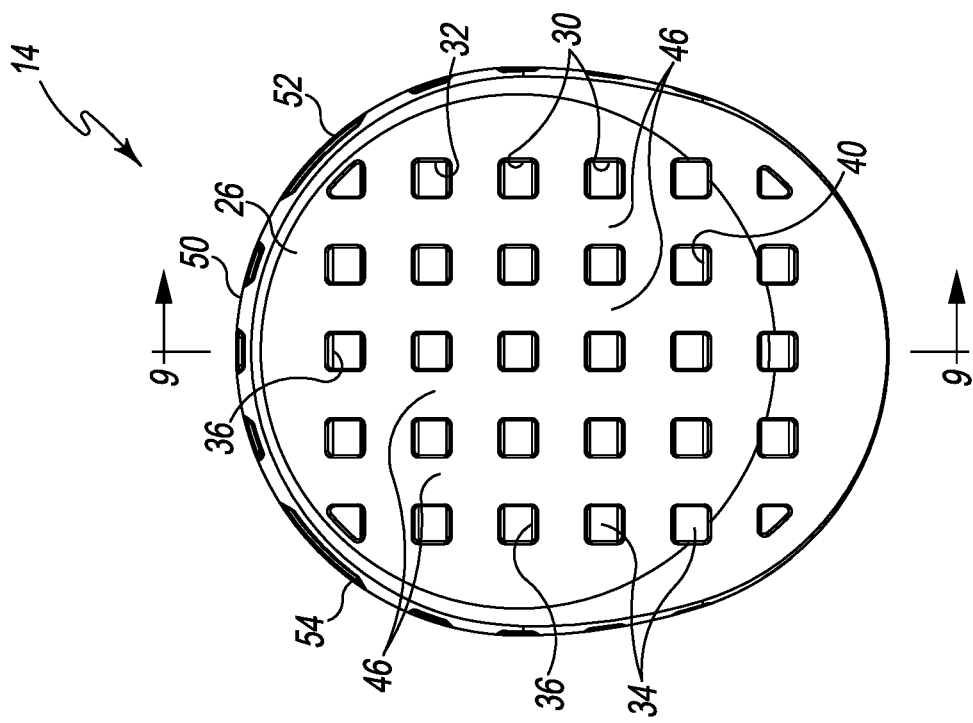
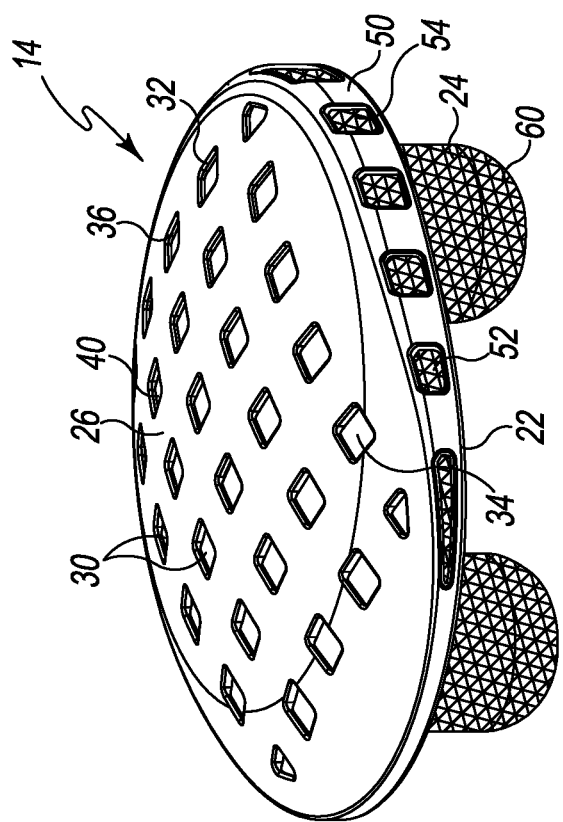

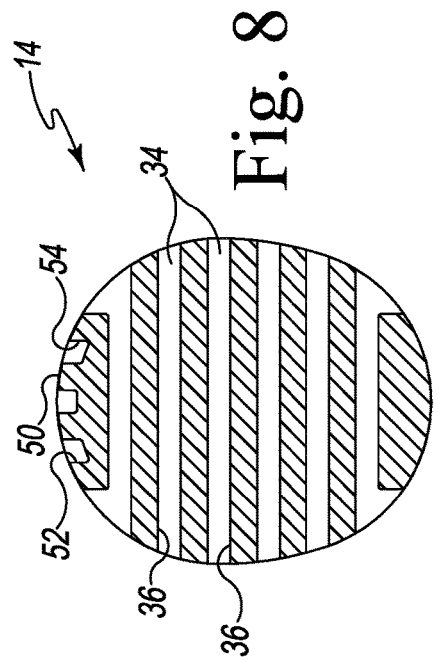
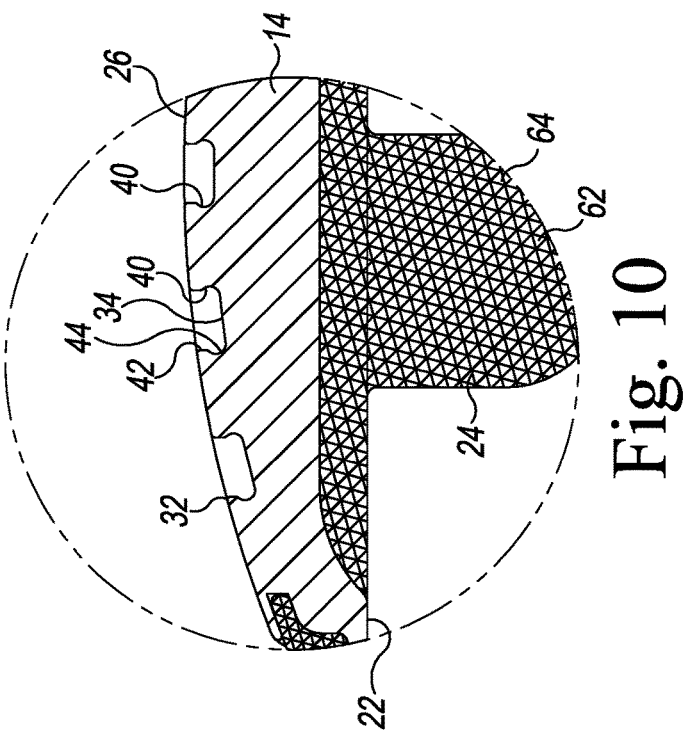
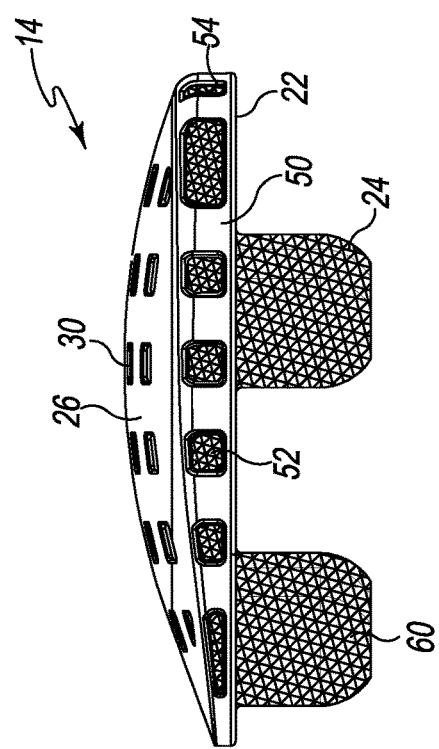
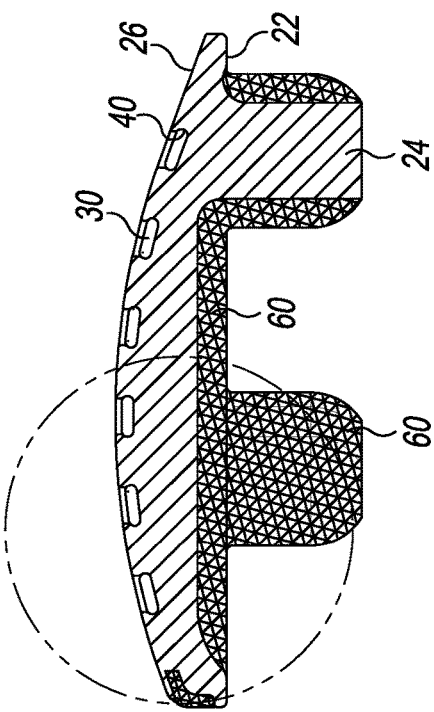

METAL-BACKED TIBIAL COMPONENT OF AN ORTHOPAEDIC KNEE PROSTHESIS AND ASSOCIATED METHOD OF MAKING THE SAME

This continuation-in-part application claims priority to U.S. patent application Ser. No. 16/717,077, which was filed on Dec. 17, 2019, the entirety of which is expressly incorporated herein by reference.

TECHNICAL FIELD

The present disclosure relates generally to an implantable orthopaedic knee prosthesis, and more particularly to an implantable tibial component of an orthopaedic knee prosthesis.

BACKGROUND

During the lifetime of a patient, it may be necessary to perform a joint replacement procedure on the patient as a result of, for example, disease or trauma. The joint replacement procedure may involve the use of a prosthesis which is implanted into one or more of the patient's bones.

In the case of a patella replacement procedure, an orthopaedic prosthesis is implanted into the patient's patella. Specifically, a prosthetic patella component is secured to the patient's natural patella such that its posterior surface articulates with a femoral component during extension and flexion of the knee.

In a knee replacement procedure, an orthopaedic prosthesis may also be implanted into the patient's tibia. Specifically, a prosthetic tibial component is secured to a surgically-prepared proximal end of the patient's natural tibia so as to articulate with a prosthetic femoral component during extension and flexion of the knee.

SUMMARY

According to an aspect of the disclosure, an orthopaedic implant includes a patella component. The patella component has a solid-metal base that includes a posterior base surface having a number of pockets formed therein. Each of the pockets has an undercut formed therein. The solid-metal base also has an anterior base surface with a number of pegs extending outwardly therefrom. A porous-metal coating is disposed on the anterior base surface and the pegs of the solid-metal base. A polymer bearing is molded to the posterior base surface of the solid-metal base. The polymer bearing has a posterior bearing surface configured to articulate with a pair of femoral condyles of a femoral component.

In an embodiment, the polymer bearing is molded into the pockets of the solid-metal base.

Illustratively, a posterior end of each of the pockets is defined by an opening formed in the posterior base surface, with an anterior end of each of the pockets being defined by a base wall that is spaced apart anteriorly from the opening. The medial and lateral sides of the pockets are defined by a pair of sidewalls that extend from the opening to the base wall. The sidewalls have the undercuts formed therein.

In an embodiment, the surfaces of the sidewalls defining the undercut have rounded surfaces.

Illustratively, a number of adjacent pockets of the solid-metal base open into one another.

In an embodiment, the solid-metal base further includes a perimeter sidewall extending between the posterior base surface and the anterior base surface. The perimeter sidewall has a number of pockets formed therein, and each of the pockets formed in the perimeter sidewall has the porous-metal coating disposed therein.

Illustratively, the patella component may be embodied as a dome patella component or an anatomic patella component.

According to another aspect, an orthopaedic implant includes a patella component. The patella component includes a solid-metal base that has a posterior base surface having a number of pockets formed therein, and an anterior base surface that has a number of pegs extending outwardly therefrom. A posterior end of each of the pockets is defined by an opening formed in the posterior base surface, with an anterior end of each of the pockets being defined by base wall that is spaced apart anteriorly from the opening. The medial and lateral sides of the pockets are defined by a pair of sidewalls that extend from the opening to the base wall. A number of adjacent pockets open into one another. A porous-metal coating is disposed on the anterior base surface and the pegs of the solid-metal base. A polymer bearing is molded to the posterior base surface of the solid-metal base. The polymer bearing has a posterior bearing surface configured to articulate with a pair of femoral condyles of a femoral component.

In an embodiment, the polymer bearing is molded into the pockets of the solid-metal base.

In an embodiment, the surfaces of the sidewalls defining the undercut have rounded surfaces.

In an embodiment, the solid-metal base further includes a perimeter sidewall extending between the posterior base surface and the anterior base surface. The perimeter sidewall has a number of pockets formed therein, and each of the pockets formed in the perimeter sidewall has the porous-metal coating disposed therein.

Illustratively, the patella component may be embodied as a dome patella component or an anatomic patella component.

According to yet another aspect of the disclosure, a method of making a patella component includes disposing a porous-metal coating onto an anterior surface and a number of pegs of a solid-metal base. A polymer bearing is molded onto a posterior surface of the solid-metal base such that a portion of an anterior surface of the polymer bearing is disposed within a number of pockets formed in the posterior surface of the solid-metal base. A posterior surface of the polymer bearing forms a patella bearing surface that is configured to articulate with a pair of femoral condyles of a femoral component.

Illustratively, the porous-metal coating and the solid-metal base is 3D-printed as a monolithic metal component.

In an embodiment, a number of sidewalls defining the pockets of the solid-metal base have undercuts formed therein. The polymer bearing is molded onto the posterior surface of the solid-metal base such that a portion of the anterior surface of the polymer bearing is molded to the sidewalls defining the undercuts of the pockets.

The polymer bearing may be molded to include either a dome patella bearing surface or an anatomic patella bearing surface, both of which are configured to articulate with the pair of femoral condyles of the femoral component.

According to another aspect, an orthopaedic implant includes a tibial component configured to be implanted on a surgically-prepared proximal end of a patient's tibia. The tibial component includes a solid-metal base that has a superior base surface having a number of pockets formed therein with each of the pockets having an undercut formed therein, and an inferior base surface having a number of pegs extending outwardly therefrom. The tibial component also has a porous-metal coating disposed on the inferior base surface and the pegs, and a polymer bearing molded to the superior base surface of the solid-metal base. The polymer bearing has a tibial bearing surface configured to articulate with a pair of femoral condyles of a femoral component.

In an embodiment, the polymer bearing is molded into the pockets of the solid-metal base.

In an illustrative embodiment, a superior end of each of the pockets is defined by an opening formed in the superior base surface, with an inferior end of each of the pockets being defined by base wall that is spaced apart inferiorly from the opening. In such an illustrative embodiment, two sides of the pockets are defined by a pair of sidewalls that extend from the opening to the base wall, with the sidewalls having the undercuts formed therein.

The surfaces of the sidewalls defining the undercut may include rounded surfaces.

In an illustrative embodiment, a number of adjacent pockets open into one another.

In an embodiment, the solid-metal base includes a perimeter sidewall extending between the superior base surface and the inferior base surface. The perimeter sidewall may have a number of pockets formed therein, with each of the pockets formed in the perimeter sidewall having the porous-metal coating disposed therein.

The tibial component may also include a polymer stem extending away from the inferior base surface of the solid-metal base.

In an embodiment, the solid-metal base has a central opening defined therein, and the polymer bearing and the polymer stem define a monolithic structure that extends through the central opening.

In an embodiment, each of the pockets of the solid-metal base has the porous-metal coating disposed therein.

According to another aspect, an orthopaedic implant includes a polymer tibial bearing having a bearing surface configured to articulate with a pair of femoral condyles of a femoral component and an inner sidewall that defines an opening therein. The orthopaedic implant also includes a tibial component configured to be implanted on a surgically-prepared proximal end of a patient's tibia. The tibial component includes a solid-metal base that includes a superior base surface that has a number of pockets formed therein with each of the pockets having an undercut formed therein, and an inferior base surface having a number of pegs extending outwardly therefrom. The tibial component also includes a porous-metal coating disposed on the inferior base surface and the pegs, and a polymer locking plate molded to the superior base surface of the solid-metal base. The polymer locking plate has a generally Y-shaped posterior buttress extending upwardly from a superior surface of the polymer locking plate. The posterior buttress is configured to be received in the opening of the tibial bearing to prevent rotation of the tibial bearing relative to the tibial component.

The polymer bearing may be molded into the pockets of the solid-metal base.

In an illustrative embodiment, a superior end of each of the pockets is defined by an opening formed in the superior base surface, with an inferior end of each of the pockets being defined by base wall that is spaced apart inferiorly from the opening. In such an illustrative embodiment, two sides of the pockets are defined by a pair of sidewalls that extend from the opening to the base wall, with the sidewalls having the undercuts formed therein.

The surfaces of the sidewalls defining the undercut may include rounded surfaces.

In an illustrative embodiment, a number of adjacent pockets open into one another.

In an embodiment, the solid-metal base includes a perimeter sidewall extending between the superior base surface and the inferior base surface. The perimeter sidewall may have a number of pockets formed therein, with each of the pockets formed in the perimeter sidewall having the porous-metal coating disposed therein.

The tibial component may also include a polymer stem extending away from the inferior base surface of the solid-metal base.

In an embodiment, the solid-metal base has a central opening defined therein, and the polymer bearing and the polymer stem define a monolithic structure that extends through the central opening.

In an embodiment, each of the pockets of the solid-metal base has the porous-metal coating disposed therein.

According to another aspect, a method of making a tibial component includes disposing a porous-metal coating onto an inferior surface and a number of pegs of a solid-metal base. A polymer bearing is molded onto a superior surface of the solid-metal base such that a portion of an inferior surface of the polymer bearing is disposed within a number of pockets formed in the superior surface of the solid-metal base. A superior surface of the polymer bearing forms a tibial bearing surface that is configured to articulate with a pair of femoral condyles of a femoral component.

Illustratively, the porous-metal coating and the solid-metal base is 3D-printed as a monolithic metal component.

In an embodiment, a number of sidewalls defining the pockets of the solid-metal base have undercuts formed therein. The polymer bearing is molded onto the superior surface of the solid-metal base such that a portion of the inferior surface of the polymer bearing is molded to the sidewalls defining the undercuts of the pockets.

Illustratively, the solid-metal base has a central opening defined therein. A polymer stem extends inferiorly away from the inferior surface of the solid-metal base such that the polymer bearing and the polymer stem define a monolithic structure that extends through the central opening.

BRIEF DESCRIPTION

The detailed description particularly refers to the following figures, in which:

FIG. 1 is a perspective view of a metal-backed dome patella component of an orthopaedic knee prosthesis;

FIG. 2 is a superior side elevation view of the metal-backed dome patella component of FIG. 1;

FIG. 3 is an anterior side elevation view of the metal-backed dome patella component of FIG. 1;

FIG. 5 is a perspective view of the solid-metal base of the metal-backed dome patella component of FIG. 1;

FIG. 6 is a posterior side elevation view of the solid-metal base of FIG. 5;

FIG. 7 is a superior side elevation view of the solid-metal base of FIG. 5;

FIG. 8 is a view similar to FIG. 6, but showing the solid-metal base having a thin layer of its posterior surface removed;

FIG. 9 is a cross-sectional view taken along the line 9-9 of FIG. 6, as viewed in the direction of the arrows, note the porous-metal coating is not shown in cross section in FIG. 9 for clarity of description;

FIG. 10 is an enlarged cross sectional view showing the pockets of the solid-metal base in greater detail, with FIG. 10 being taken from FIG. 9 as indicated by the encircled area;

DETAILED DESCRIPTION

Figure 4:
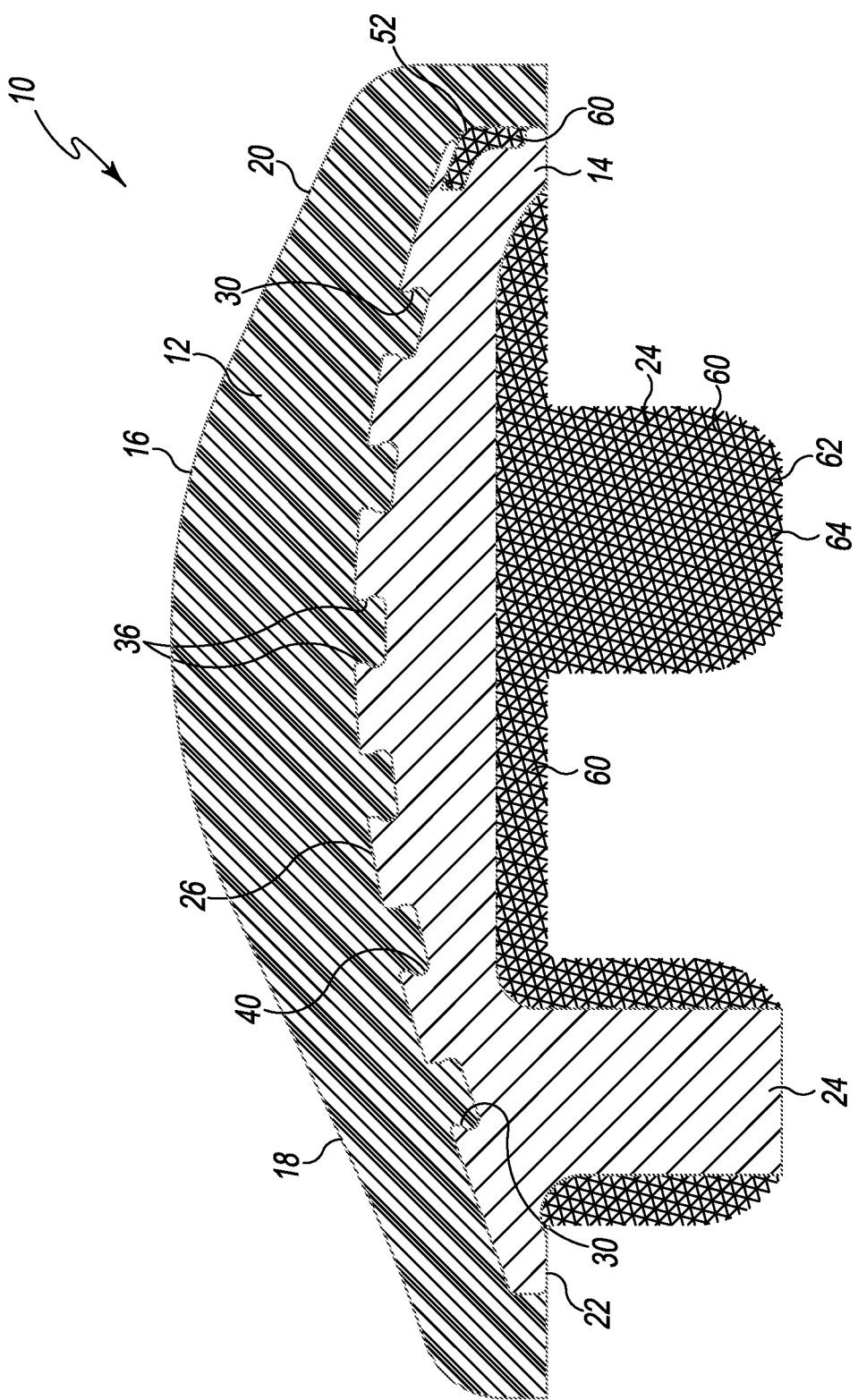
FIG. 4 is an cross-sectional view taken along the line 4-4 of FIG. 3, as viewed in the direction of the arrows, note the porous-metal coating is not shown in cross section in FIG. 4 for clarity of description.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIGS. 1-4, there is shown a metal-backed dome patella component 10 of an implantable knee prosthesis. As will be described in greater detail below, the dome patella component 10 includes a polymer bearing 12 molded onto a solid-metal base 14 so as to create a one-piece (i.e., non-modular) final product. The polymer bearing 12 of the dome patella component 10 includes a posterior bearing surface 16 configured to articulate with a pair of condylar surfaces of a femoral component (not shown) that has been secured to a surgically-prepared end of a patient's distal femur (not shown). In particular, the posterior bearing surface 16 of the dome patella component 10 includes a lateral articular surface 18 and a medial articular surface 20. The articular surfaces 18, 20 are configured to articulate with a lateral condyle surface and a medial condyle surface, respectively, of the femoral component (not shown). It should be appreciated that such a femoral component is configured to emulate the configuration of the patient's natural femoral condyles, and, as such, the lateral condyle surface and the medial condyle surface of the prosthetic femoral component are configured (e.g., curved) in a manner which mimics the condyles of the natural femur.

As can be seen in FIGS. 2-4, solid-metal base 14 of the dome patella component 10 includes a generally flat anterior surface 22 having a number of fixation members, such as pegs 24, extending outwardly therefrom. The pegs 24 are configured to be implanted into a surgically prepared posterior surface of the patient's natural patella (not shown). In such a way, the posterior bearing surface 16 of the dome patella component 10 faces toward the femoral component thereby allowing the posterior bearing surface 16 to articulate with the femoral condyle surfaces thereof during flexion and extension of the patient's knee.

The polymer bearing 12 of the dome patella component 10 is embodied as a monolithic polymer body constructed with a material that allows for smooth articulation between the patella component 10 and the femoral component (which is generally constructed with a biocompatible metal, such as a cobalt chrome alloy, although other materials, such as ceramics, may also be used). One such polymeric material is polyethylene such as ultrahigh molecular weight polyethylene (UHMWPE).

Referring now to FIGS. 4-10, the solid-metal base 14 is shown in more detail. Opposite its anterior surface 22, the solid-metal base 14 includes a rounded posterior surface 26 onto which the polymer bearing 12 is molded. The posterior surface 26 has a number of pockets 30 formed therein. As will be discussed below, the pockets 30 allow for polymer interdigitation during molding of the molded polymer bearing 12 onto the solid-metal base 14. As can be seen in FIG. 6, in the illustrative embodiment described herein, the pockets 30 are arranged in the posterior surface 26 in a cross-hatch type pattern although other patterns may also be used. As can be seen in FIGS. 4, 9, and 10, a posterior end of each of the pockets 30 is defined by an opening 32 formed in the posterior surface 26, with the pocket's opposite anterior end being defined by base wall 34. The base wall 34 is spaced apart anteriorly from the opening 32 toward the center of the body of the solid-metal base 14. The medial and lateral sides of the pockets 30 are defined by a pair of sidewalls 36 that extend from the opening 32 to the base wall 34.

As can be seen in FIGS. 4, 9, and 10, each of the pockets 30 has an undercut 40 formed therein. Specifically, the base walls 34 defining the anterior ends of each of the pockets 30 is wider than the openings 32 defining the posterior ends of each of the pockets 30. The sidewalls 36 extend away from the openings 32 along a convex surface 42 that transitions to a concave surface 44 prior transitioning to the base wall 34 thereby creating the undercuts 40. It should be appreciated that although the undercuts 40 are shown as blended-radius undercuts 40 (i.e., the surfaces defining the undercuts are rounded), other configurations are also contemplated including, for example, undercuts that that are more squared off in design (e.g., the sidewalls 36 define orthogonal transitions instead of rounded transitions).

As can be seen in FIG. 4, the sidewalls 36 defining the undercuts 40 create a surface that faces away from the outer posterior surface 26 of the solid-metal base 14 to which the polymer bearing 12 is molded. In such a way, the undercuts 40 resist pull-off of the polymer bearing 12 from the solid-metal base 14.

As can be seen in FIG. 8, the adjacent pockets 30 of a given row of the cross-hatch pattern open into one another. In particular, as can be seen the context of FIG. 8 in which a thin outer layer of the posterior surface 26 of the solid-metal base 14 has been removed, the base wall 34 of a given row of pockets 30 extends across much of the width of the solid-metal base 14. Although the sidewalls 36 close a given pocket 30 in the medial/lateral direction, there are no sidewalls positioned between the pockets 30 of a given row extending in the superior/inferior direction. As such, adjacent pockets 30 within such a row extending in the superior/inferior direction open into one another thereby allowing polymer material to be advanced between the adjacent pockets 30 and therefore under the sections 46 of the posterior surface 26 between the pockets 30. The underside of the sections 46 creates a surface that faces away from the outer posterior surface 26 of the solid-metal base 14 to which the polymer bearing 12 is molded. In such a way, the underside of the sections 46 resist pull-off of the polymer bearing 12 from the solid-metal base 14.

As can be seen in FIGS. 5 and 7, an outer perimeter sidewall 50 extends between the posterior surface 26 of the solid-metal base 14 and its anterior surface 22. Because the dome patella component 10 is embodied as a medially-offset dome patella component 10, the perimeter sidewall 50 is wider at the medial side of the solid-metal base 14 than it is at the lateral side of the solid-metal base 14. As can be seen in FIGS. 5-7, the superior, inferior, and medial sides of the perimeter sidewall 50 have a number of wall pockets 52 formed therein. The wall pockets 52 extend inwardly into the center of the solid-metal base 14 from openings 54 formed in the perimeter sidewall 50. Like the pockets 30 formed in the posterior surface 26 of the solid-metal base 14, the wall pockets 52 allow for polymer interdigitation into the solid-metal base 14 during molding of the molded polymer bearing 12 onto the solid-metal base 14.

As can be seen in FIGS. 2-5, the anterior surface 22 and the pegs 24 of the solid-metal base 14 have a porous-metal coating 60 disposed thereon. As can be seen in FIGS. 5 and 7, the porous-metal coating 60 may also be disposed in the wall pockets 50 of the solid-metal base 14. It should be appreciated that the porous-metal coating 60 could be a separately-applied coating such as Porocoat® Porous Coating which is commercially available from DePuy Synthes of Warsaw, Indiana. However, in the illustrative embodiment described herein, the porous-metal coating 60 is disposed on the solid-metal base 14 by virtue of being additively manufactured contemporaneously with the solid-metal base 14 so as to create a common, monolithic component of the two metal structures.

In one example, the porous-metal coating 60 may be made of a porous material 62 as described in U.S. patent application Ser. No. 16/365,557, which was filed Mar. 26, 2019 and is assigned to the same assignee as the present disclosure, the disclosure of which is hereby incorporated by reference as if set forth in its entirety herein. Additive manufacturing processes can include, by way of example, powder bed fusion printing, such as melting and sintering, cold spray 3D printing, wire feed 3D printing, fused deposition 3D printing, extrusion 3D printing, liquid metal 3D printing, stereolithography 3D printing, binder jetting 3D printing, material jetting 3D printing, and the like.

In one example, referring to FIG. 4, the porous material 62 of the porous-metal coating 60 can be defined by a porous three-dimensional structure that includes a plurality of connected unit cells. Each unit cell can define a unit cell structure 64 that includes a plurality of lattice struts that define an outer geometric structure and a plurality of internal struts that define a plurality of internal geometric structures that are disposed within the outer geometric structure. In one example, the outer geometric structure may be a rhombic dodecahedron, and the inner geometric structures may be a rhombic trigonal trapezohedron. It should be appreciated that such geometric structures may vary to fit the needs of a given design. Further, it should be appreciated that the unit cells that make up the porous-metal coating 60 may also have any suitable alternative geometry to fit the needs of a given design.

The porous material 62 is formed from a metal powder. Illustratively, the metal powders may include, but are not limited to, titanium, titanium alloys, stainless steel, cobalt chrome alloys, tantalum, or niobium powders. The porous-metal coating 60 has a porosity suitable to facilitate bony ingrowth into the dome patella component 10 when the anterior surface 22 and the pegs 24 of the solid-metal base 14 are implanted into the surgically-prepared posterior surface of the patient's patella.

In the illustrative embodiment described herein, the porous-metal coating 60 is additively manufactured directly onto the anterior surface 22 and the pegs 24, and into wall pockets 50, of the solid-metal base 14. In such an embodiment, the two structures—i.e., the solid-metal base 14 and the porous-metal coating 60—may be manufactured contemporaneously during a common additive manufacturing process. For example, the two structures may be manufactured contemporaneously in a single 3D printing operation that yields a common, monolithic metallic component including both structures. Alternatively, the porous-metal coating 60 could be manufactured as a separate component that is secured to the solid-metal base 14.

The polymer bearing 12 may be assembled to the solid-metal base 14 by use of a number of different techniques. One exemplary manner for doing so is by use of compression molding techniques. For example, the solid-metal base 14 and the material from which the polymer bearing 12 is to be made (e.g., UHMWPE) may be placed in a mold with one another. Thereafter, the components are compression molded to one another under process parameters which cause the material from which the polymer bearing 12 is made (e.g., UHMWPE) to be molten and mechanically secured to the solid-metal base 14 by the compression molding process. As described above, the molten polymer bearing 12 interdigitates with the pockets 30, 52 of the solid-metal base 14 when molded thereto. It should also be appreciated that the mold may be configured to not only mold the components to one another, but also form the posterior bearing surface 16 into the polymer bearing 12.

The starting materials (e.g., polymers such as polyethylene) for use in the molding process may be provided in a number of different forms. For example, each of the starting materials may be provided as a preform. What is meant herein by the term "preform" is an article that has been consolidated, such as by ram extrusion or compression molding of polymer resin particles, into rods, sheets, blocks, slabs, or the like. The term "preform" also includes a preform "puck" which may be prepared by intermediate machining of a commercially available preform. Polymer preforms such as polyethylene preforms may be provided in a number of different pre-treated or preconditioned variations. For example, crosslinked or non-crosslinked (e.g., irradiated or non-irradiated) preforms may be utilized. Such preforms may be treated to eliminate (e.g., re-melting or quenching) or stabilize (e.g., the addition of vitamin E as an antioxidant) any free radicals present therein. Alternatively, the preforms may not be treated in such a manner.

The starting materials (e.g., polymers and copolymers) may also be provided as powders. What is meant herein by the term "powder" is resin particles. Similarly to as described above in regard to preforms, powders may be provided in a number of different pre-treated or preconditioned variations. For example, crosslinked or non-crosslinked (e.g., irradiated or non-irradiated) powders may be utilized.

Figure 11:
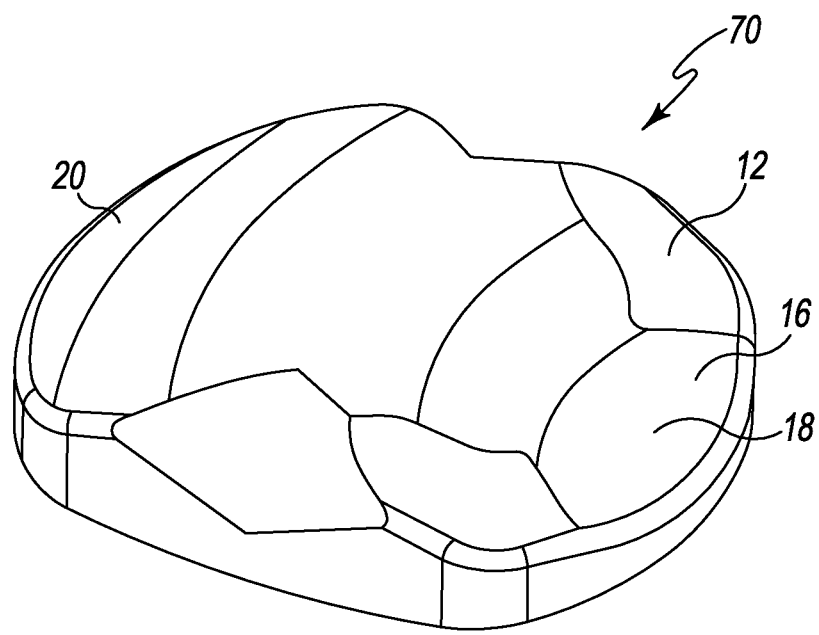
FIG. 11 is a view similar to FIG. 1, but showing a metal-backed anatomic patella component of an orthopaedic knee prosthesis.
Figure 12:
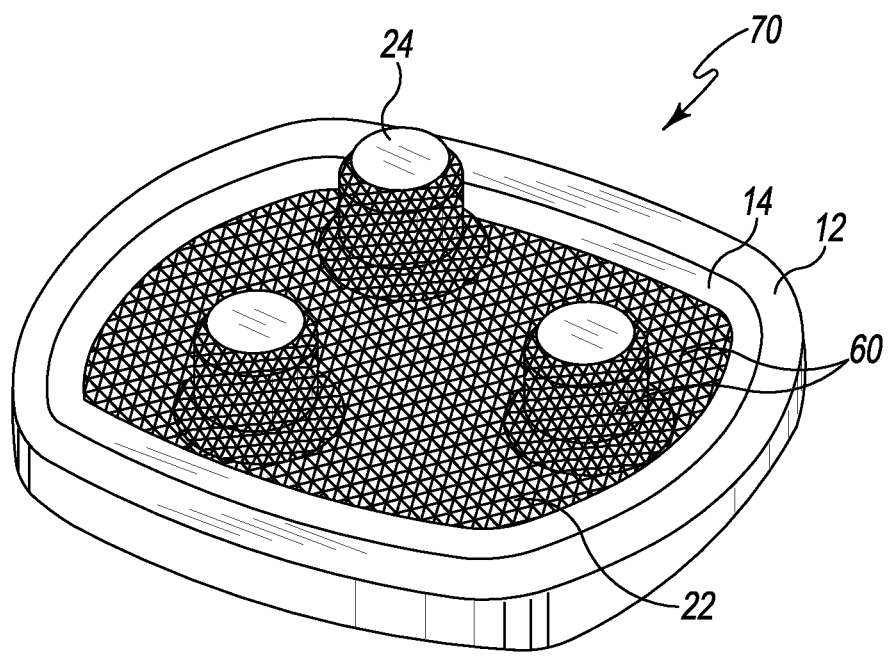
FIG. 12 is a perspective view of the anterior side of the metal-backed anatomic patella component of FIG. 11.

As shown in FIGS. 11 and 12, although the concepts of the present disclosure have herein been described in the context of the dome patella component 10, it should be appreciated that the concepts of the present disclosure may also be used in the design of an anatomic component 70. It is further contemplated that a common design of a solid-metal base 14 may be used for both a dome patella component and an anatomic patella component. In such an arrangement, the same solid-metal base 14 would be used with the resultant type of component be determined by the configuration of the mold used to form the polymer bearing 12.

Figure 14:
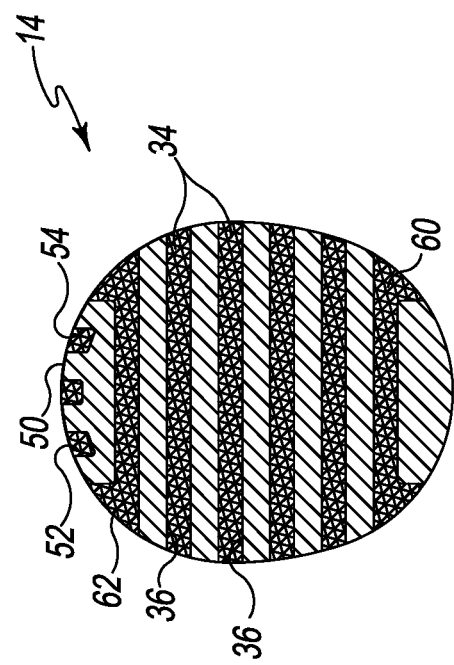
FIG. 14 is a view similar to FIG. 8, but showing the solid-metal base of the metal-backed dome patella component of FIG. 1 having the porous-metal coating disposed in its pockets.
Figure 13:
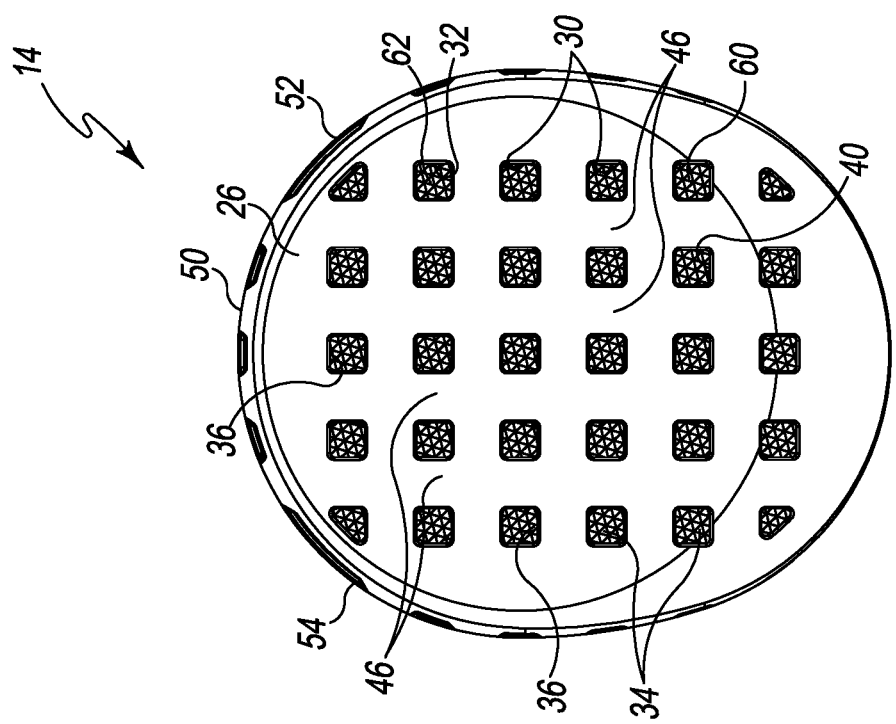
FIG. 13 is a view similar to FIG. 6, but showing the solid-metal base of the metal-backed dome patella component of FIG. 1 having the porous-metal coating disposed in its pockets.
Figure 15:
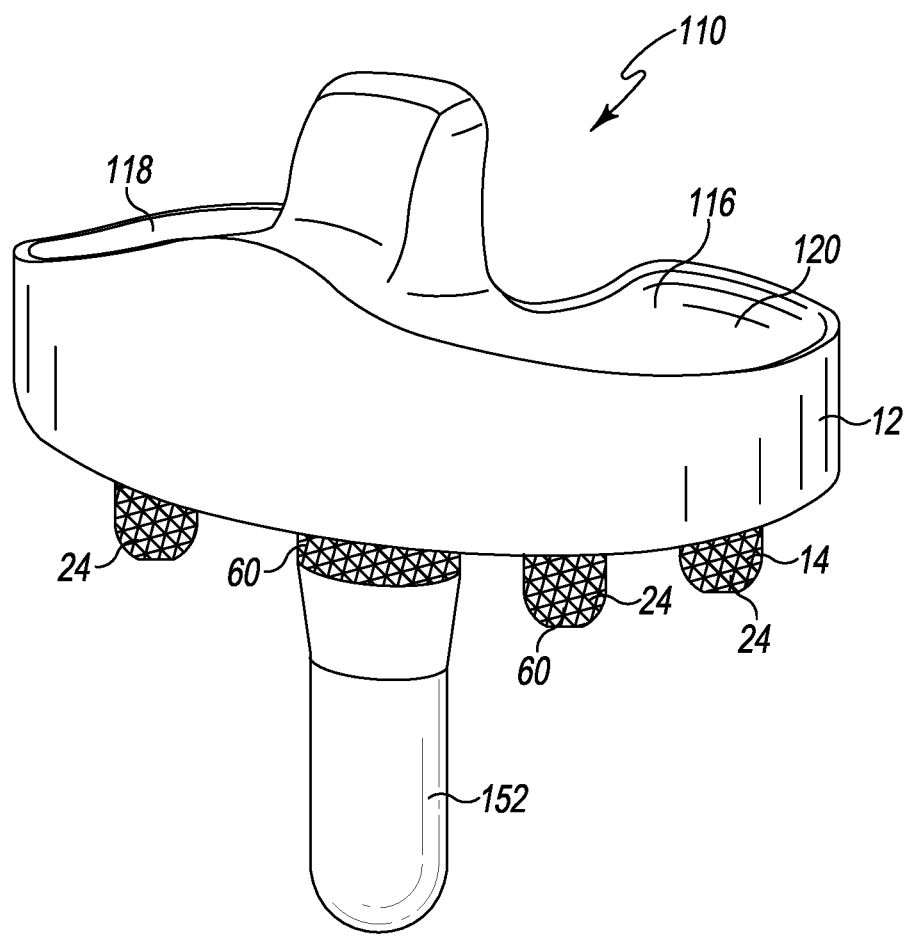
FIG. 15 is a perspective view of a metal-backed tibial component of an orthopaedic knee prosthesis.
Figure 16:
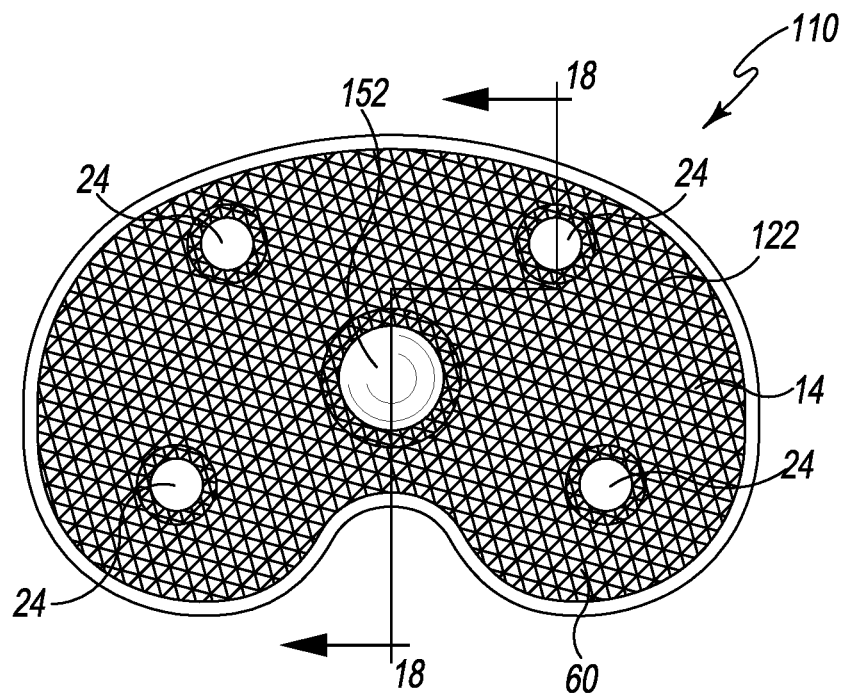
FIG. 16 is a inferior side elevation view of the metal-backed tibial component of FIG. 15.
Figure 17:
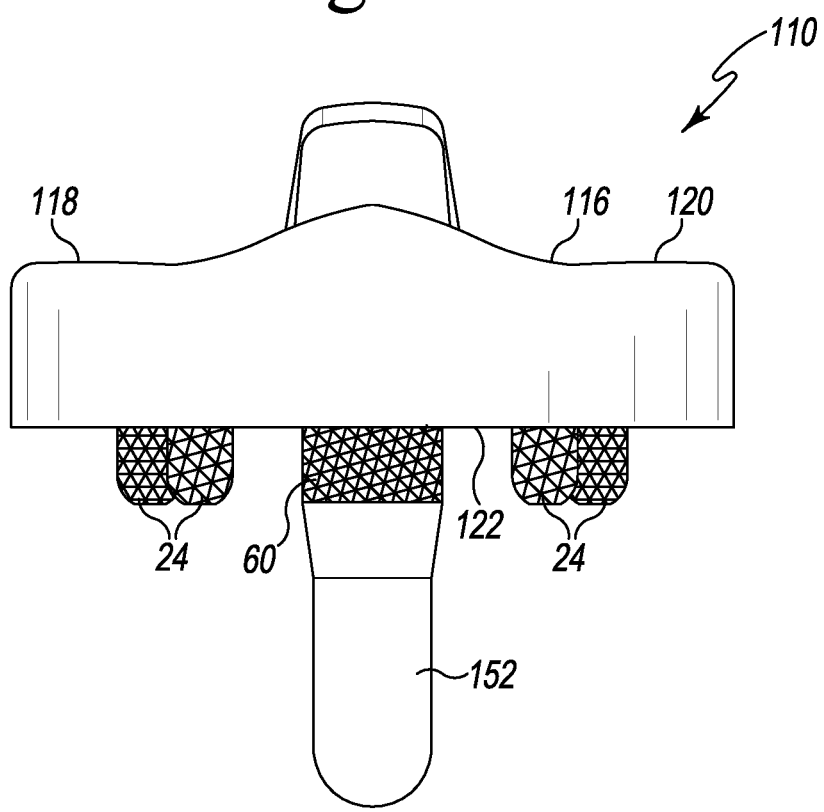
FIG. 17 is an anterior side elevation view of the metal-backed tibial component of FIG. 15.

As shown in FIGS. 13 and 14, the porous-metal coating 60 may be disposed in additional locations of the solid-metal base 14. For example, the porous-metal coating 60 may be disposed in the pockets 30, including the open areas between adjacent pockets 30 (i.e., the areas under the sections 46 of the posterior surface 26 between the pockets 30). In such an embodiment, the molten polymer material (e.g., UHMWPE) would not only interdigitate with the structures defining the pockets 30, but also the porous-metal coating 60 within the pockets 30 when the polymer bearing 12 is molded to the solid-metal base 14.

It should be appreciated that the concepts of the present disclosure may be utilized in the design of other types of orthopaedic implants. For example, as shown in FIGS. 15-20, the concepts of the present disclosure may be utilized in the design of a metal-backed tibial component 110 of an implantable knee prosthesis. The tibial component 110 incorporates many of the same features and structures as the patella component 10 described above. As such, the same reference numerals are utilized in FIGS. 15-20 to designate features and structures that have previously been discussed in regard to FIGS. 1-14, with additional discussion thereof being unwarranted.

As will be described in greater detail below, the tibial component 110 includes a polymer bearing 12 molded onto a solid-metal base 14 so as to create a one-piece (i.e., non-modular) final product. The polymer bearing 12 of the tibial component 110 includes a tibial bearing surface 116 configured to articulate with a pair of condylar surfaces of a femoral component (not shown) that has been secured to a surgically-prepared end of a patient's distal femur (not shown). In particular, the tibial bearing surface 116 of the tibial component 110 includes a lateral articular surface 118 and a medial articular surface 120. The articular surfaces 118, 120 are configured to articulate with a lateral condyle surface and a medial condyle surface, respectively, of the femoral component (not shown). Similarly to as noted above, it should be appreciated that such a femoral component is configured to emulate the configuration of the patient's natural femoral condyles, and, as such, the lateral condyle surface and the medial condyle surface of the prosthetic femoral component are configured (e.g., curved) in a manner which mimics the condyles of the natural femur.

Figure 18:
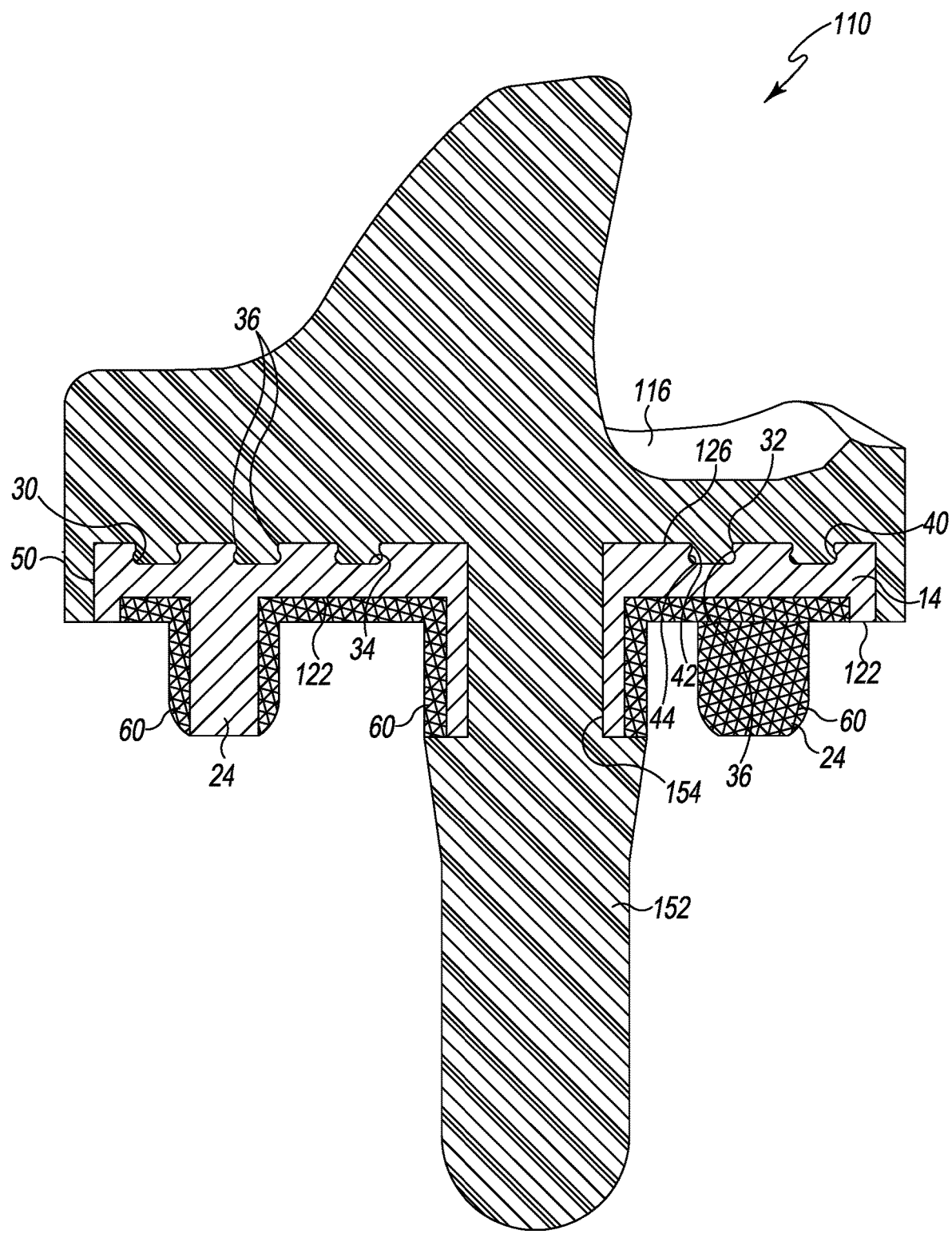
FIG. 18 is an cross-sectional view taken along the line 18-18 of FIG. 16, as viewed in the direction of the arrows, note the porous-metal coating is not shown in cross section in FIG. 18 for clarity of description.
Figure 19:
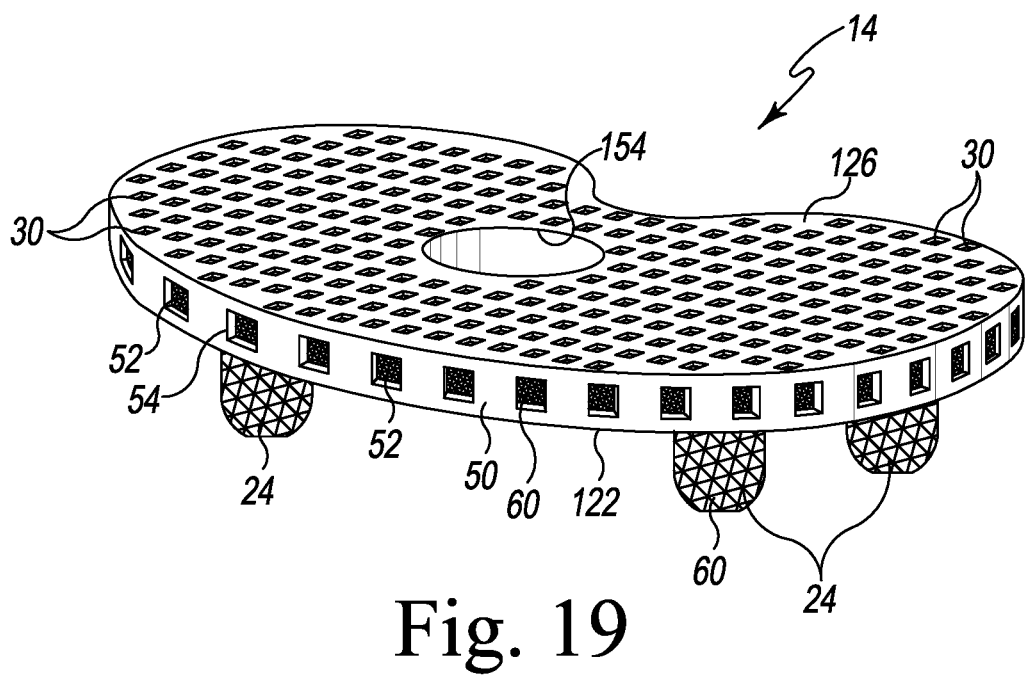
FIG. 19 is a perspective view of the solid-metal base of the metal-backed tibial component of FIG. 15.
Figure 20:
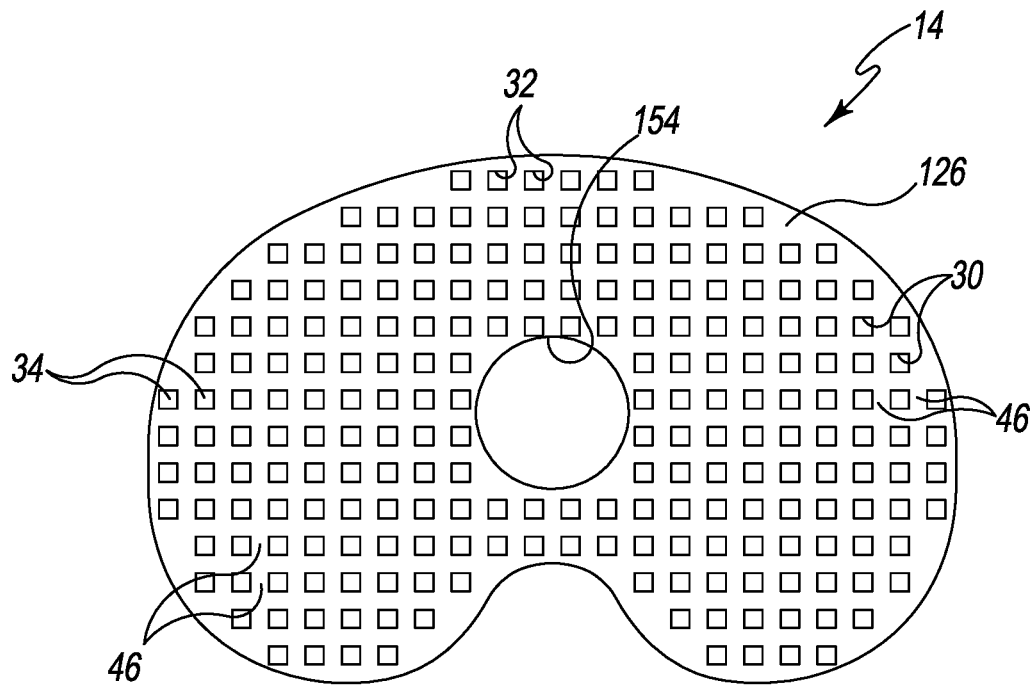
FIG. 20 is a superior side elevation view of the solid-metal base of FIG. 19.

As can be seen in FIGS. 18-20, the solid-metal base 14 of the tibial component 110 includes a generally flat inferior surface 122 having a number of fixation members, such as pegs 24, extending outwardly therefrom. The pegs 24 are configured to be implanted into a surgically-prepared proximal surface of the patient's natural tibia (not shown). In such a way, the tibial bearing surface 116 of the tibial component 110 faces toward the femoral component thereby allowing the tibial bearing surface 116 to articulate with the femoral condyle surfaces thereof during flexion and extension of the patient's knee. It should be appreciated that the pegs 24 prevent rotation of the tibial component 110 relative to the patient's tibia once it is implanted therein. It should also be appreciated that the pegs 24 may be embodied as other structures, such as keels, for preventing such rotation.

Like the polymer bearing 12 of the patella component 10, the polymer bearing 12 of the tibial component 110 is embodied as a monolithic polymer body constructed with a material that allows for smooth articulation between the tibial component 110 and the femoral component (which is generally constructed with a biocompatible metal, such as a cobalt chrome alloy, although other materials, such as ceramics, may also be used). Any of the materials discussed above in regard to the patella component 10, such as ultrahigh molecular weight polyethylene (UHMWPE), may be used in the construction of the polymer bearing 12 of the tibial component 110. Moreover, the polymer bearing 12 of the tibial component 110 may be formed in a similar manner and from similar starting materials as described above in regard to the polymer bearing 12 of the patella component 10.

Referring now to FIGS. 18-20, the solid-metal base 14 of the tibial component 110 is shown in more detail. Opposite its inferior surface 122, the solid-metal base 14 includes a generally planar superior surface 126 onto which the polymer bearing 12 is molded. The superior surface 126 has a number of the pockets 30 formed therein. Similarly to as discussed above in regard to the patella component 10, the pockets 30 allow for polymer interdigitation during molding of the tibial polymer bearing 12 onto the solid-metal base 14 of the tibial component. As can be seen in FIG. 20, in the illustrative embodiment described herein, the pockets 30 are arranged in the superior surface 126 in a cross-hatch type pattern although other patterns may also be used. Similarly to as described above in regard to the patella component 10, a superior end of each of the pockets 30 is defined by an opening 32 formed in the superior surface 126, with the pocket's opposite inferior end being defined by the base wall 34. The base wall 34 is spaced apart inferiorly from the opening 32 toward the center of the body of the solid-metal base 14. The sides of the pockets 30 are defined by the pair of sidewalls 36 that extend from the opening 32 to the base wall 34.

In a similar manner to the patella component 10, and as can be seen in FIG. 18, each of the pockets 30 of the tibial component has an undercut 40 formed therein. Specifically, the base walls 34 defining the inferior ends of each of the pockets 30 is wider than the openings 32 defining the superior ends of each of the pockets 30. As was the case with the patella component 10, the sidewalls 36 of the tibial component 110 extend away from the openings 32 along the convex surface 42 that transitions to the concave surface 44 prior transitioning to the base wall 34 thereby creating the undercuts 40. It should be appreciated that although the undercuts 40 are shown as blended-radius undercuts 40 (i.e., the surfaces defining the undercuts are rounded), other configurations are also contemplated including, for example, undercuts that that are more squared off in design (e.g., the sidewalls 36 define orthogonal transitions instead of rounded transitions).

As can be seen in FIG. 18, the sidewalls 36 defining the undercuts 40 create a surface that faces away from the outer superior surface 26 of the solid-metal base 14 to which the polymer bearing 12 of the tibial component 110 is molded. In such a way, the undercuts 40 resist pull-off of the polymer bearing 12 from the solid-metal base 14 of the tibial component 110.

Similarly to as discussed above in regard to FIG. 8, the adjacent pockets 30 of a given row of the cross-hatch pattern of the tibial component 110 open into one another. In particular, in a similar manner to as described above in regard to FIG. 8, the base wall 34 of a given row of pockets 30 of the tibial component 110 extends across much of the width of the solid-metal base 14. As such, adjacent pockets 30 open into one another thereby allowing polymer material to be advanced between the adjacent pockets 30 and therefore under the sections 46 of the superior surface 126 between the pockets 30. The underside of the sections 46 creates a surface that faces away from the outer superior surface 126 of the solid-metal base 14 to which the polymer bearing 12 of the tibial component 110 is molded. In such a way, the underside of the sections 46 resist pull-off of the polymer bearing 12 of the tibial component 110 from its solid-metal base 14.

As can be seen in FIG. 19, the outer perimeter sidewall 50 extends between the superior surface 126 of tibial component's solid-metal base 14 and its inferior surface 122. The sides of the perimeter sidewall 50 have a number of the wall pockets 52 formed therein. The wall pockets 52 extend inwardly into the center of the solid-metal base 14 from openings 54 formed in the perimeter sidewall 50. Like the pockets 30 formed in the superior surface 126 of the solid-metal base 14, the wall pockets 52 allow for polymer interdigitation into the solid-metal base 14 during molding of the molded polymer bearing 12 onto the solid-metal base 14.

As can be seen in FIGS. 15-19, like the patella component 10, the inferior surface 122 and the pegs 24 of the tibial component's solid-metal base 14 have the porous-metal coating 60 disposed thereon. As can be seen in FIG. 19, the porous-metal coating 60 may also be disposed in the wall pockets 50 of the solid-metal base 14. It should be appreciated that any of the materials discussed above in regard to the porous-metal coating 60 of the patella component 10 may be used in the construction of the porous-meal coating 60 of the tibial component 110. Moreover, the porous-metal coating 60 of the tibial component 110 may be formed in a similar manner and from similar starting materials as described above in regard to the porous-metal coating 60 of the patella component 10.

As was the case with the patella component 10, in the illustrative embodiment described herein, the porous-metal coating 60 is additively manufactured directly onto the inferior surface 122 and the pegs 24, and into wall pockets 50, of the solid-metal base 14. In such an embodiment, the two structures—i.e., the solid-metal base 14 and the porous-metal coating 60—may be manufactured contemporaneously during a common additive manufacturing process. For example, the two structures may be manufactured contemporaneously in a single 3D printing operation that yields a common, monolithic metallic component including both structures. Alternatively, the porous-metal coating 60 could be manufactured as a separate component that is secured to the solid-metal base 14.

As can be seen in FIGS. 15-18, the tibial component 110 has a fixation member, such as an elongated polymer stem 152, extending away from the inferior surface 122 of the solid-metal base 14. The elongated polymer stem 152 is configured to be implanted into the surgically-prepared end of the patient's tibia. The polymer stem 152 may be commonly formed with the polymer bearing 12 of the tibial component to form a monolithic structure. In particular, as can be seen in FIGS. 18-20, the solid-metal base 14 has a central opening 154 formed therein. A common molding process, such as any of the molding processes described above in regard to the patella component 10, may be used to contemporaneously form the polymer bearing 12 and the polymer stem 152 with the two structures being secured to one another by polymer extending through the central opening 154.

Figure 21:
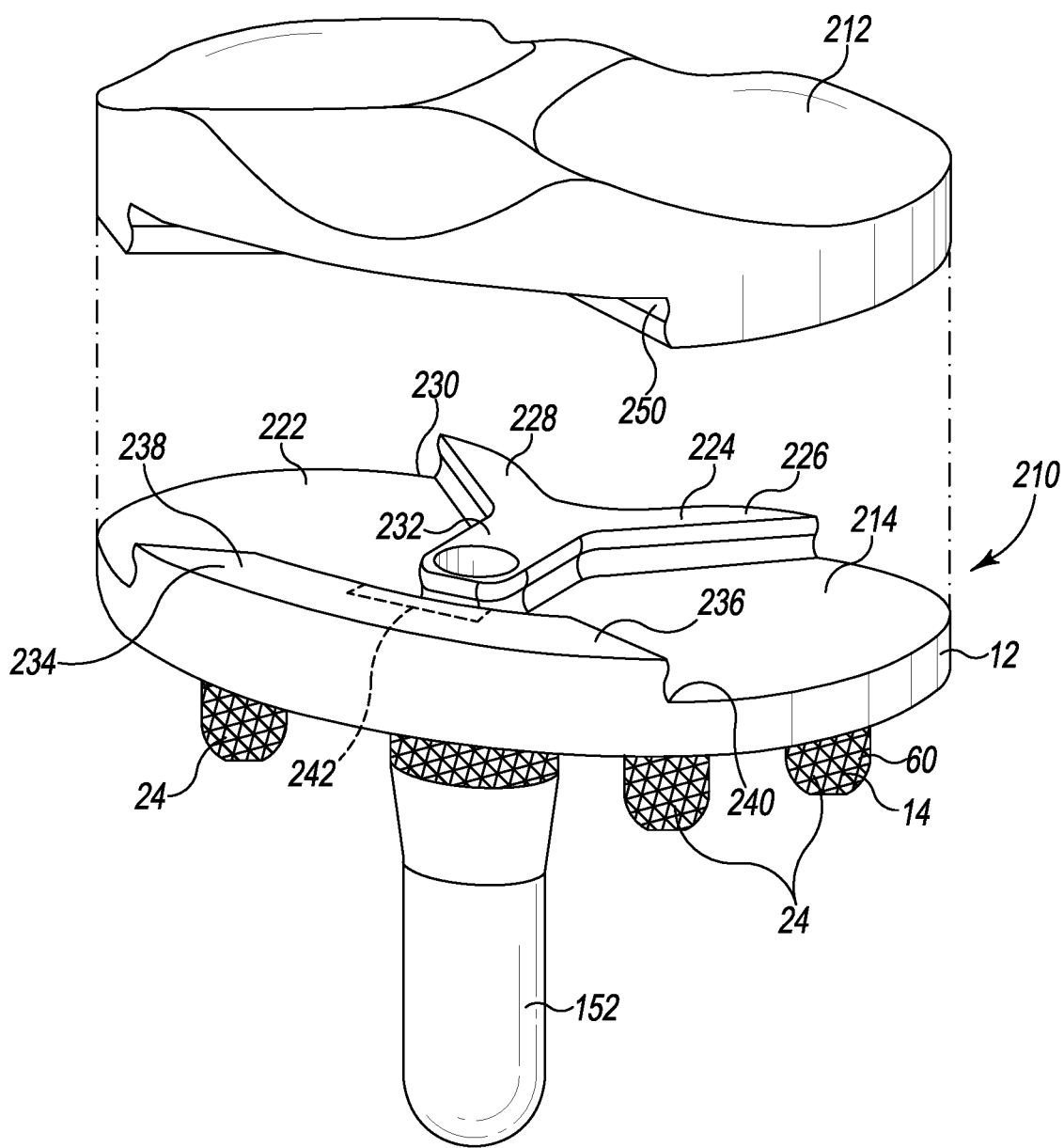
FIG. 21 is an exploded perspective view of another embodiment of a metal-backed tibial component along with a separately-attached tibial polymer bearing.
Figure 22:
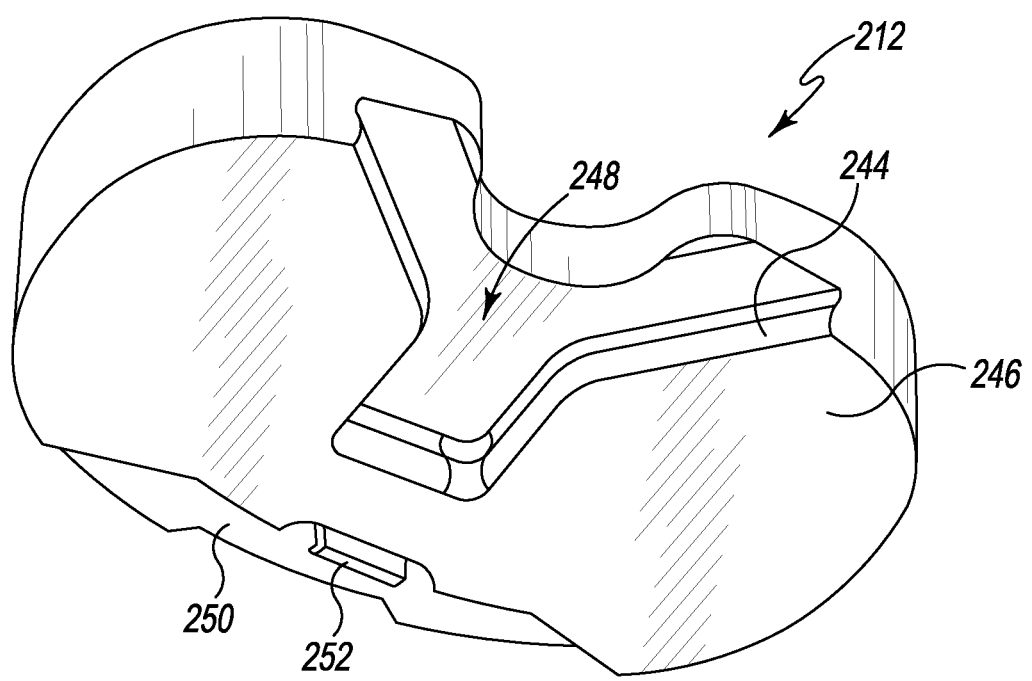
FIG. 22 is an inferior perspective view of the separately-attached tibial polymer bearing of FIG. 21.

Another embodiment of a tibial component 210 is shown in FIGS. 21 and 22. The tibial component 210 incorporates many of the same features and structures as the patella component 10 and the tibial component 110 described above. As such, the same reference numerals are utilized in FIGS. 21 and 22 to designate features and structures that have previously been discussed in regard to FIGS. 1-20, with additional discussion thereof being unwarranted.

The tibial component 210 is essentially the same as the tibial component 110 except for the configuration of the polymer structure molded to the superior surface 126 of tibial component's solid-metal base 14. Specifically, in lieu of molding the polymer bearing 12 and its tibial bearing surface 116 (including the articular surfaces 118, 120) onto the superior surface 126 of tibial component's solid-metal base 14, the tibial component 210 is configured for use with a separately-attached tibial polymer bearing 212.

To accommodate the separately-attached tibial polymer bearing 212, a polymer locking plate 214 is molded to the superior surface 126 of tibial component's solid-metal base 14. The polymer locking plate 214 has features and structures formed therein which both lock the separately-attached tibial polymer bearing 212 to the tibial component 210 and prevent it from rotating relative to the component 210. In particular, as shown in FIG. 21, a generally Y-shaped posterior buttress 224 extends upwardly from a superior surface 222 of the polymer locking plate 214. In the illustrative embodiment described herein, the posterior buttress 224 has a pair of arms 226, 228 extending along a posterior section of the perimeter of tibial component's locking plate 214. Specifically, the lateral arm 226 of the posterior buttress 224 extends along the posterior edge 230 on the lateral side of the locking plate 214, whereas the medial arm 228 of the posterior buttress 224 extends along the posterior edge 230 on the medial side of the locking plate 214 in a direction away from the lateral arm 226. A third arm 232 of the posterior buttress 224 extends anteriorly away from the intersection of the lateral arm 226 and the medial arm 228 (i.e., in a direction toward the center of the locking plate 214). In the illustrative embodiment described herein, the angle formed by the lateral arm 226 and the medial arm 228 may have a magnitude of between 45 and 145 degrees, thereby giving the posterior buttress 224 its generally Y-shape.

As also shown in FIG. 21, an anterior buttress 234 extends upwardly from the superior surface 222 of the of the polymer locking plate 214. In the illustrative embodiment described herein, the anterior buttress 234 has a pair of arms 236, 238 extending along an anterior section of the perimeter of tibial component's polymer locking plate 214. Specifically, the lateral arm 236 of the anterior buttress 234 extends along the anterior edge 240 on the lateral side of the polymer locking plate 214, whereas the medial arm 238 of the anterior buttress 234 extends along the anterior edge 240 on the medial side of the polymer locking plate 214 in a direction away from the lateral arm 236. As can be seen in FIG. 21, the anterior buttress 234 has a locking slot 242 formed therein near its medial/lateral center.

As can be seen in FIG. 22, the separately-attached tibial polymer bearing 212 has an inner sidewall 244 formed in its inferior surface 246. The inner sidewall 244 defines an opening 248 that is configured to receive the posterior buttress 224 of the tibial component's polymer locking plate 214. Likewise, the inferior surface 246 of the separately-attached tibial polymer bearing 212 has an anterior recess 250 formed therein. A locking tab 252 is positioned in the anterior recess 250 such that it is received into the locking slot 242 of the anterior buttress 234 of the tibial component's polymer locking plate 214 when the separately-attached tibial polymer bearing 212 is secured to the tibial component 210 thereby locking the two components to one another.

As with the patella component 10 and the tibial component 110, the polymer components of the tibial component 210 may be constructed of any suitable polymer. In the illustrative embodiment described herein, the polymer components of the tibial component 210 (i.e., the polymer locking plate 214 and the polymer stem 152) may be constructed with polyetheretherketone (PEEK) or polyaryletherketone (PAEK). The separately-attached tibial polymer bearing 212 may likewise be constructed of any suitable polymer such as ultrahigh molecular weight polyethylene (UHMWPE). Moreover, the polymer components of the tibial component 210 (i.e., the polymer locking plate 214 and the polymer stem 152) and the separately-attached tibial polymer bearing 212 may be formed in a similar manner and from similar starting materials as described above in regard to the polymer bearing 12 of the patella component 10 and the polymer bearing 12 of the tibial component 110.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic implant, comprising:
a tibial component configured to be implanted on a surgically-prepared proximal end of a patient's tibia, the tibial component comprising:
a solid-metal base comprising (i) a superior base surface having a number of pockets formed therein with each of the pockets having an undercut formed therein, and (ii) an inferior base surface having a number of pegs extending outwardly therefrom,
a porous-metal coating disposed on the inferior base surface and the pegs, and
a polymer bearing molded to the superior base surface of the solid-metal base, the polymer bearing having a tibial bearing surface configured to articulate with a pair of femoral condyles of a femoral component,
wherein (i) the solid-metal base further comprises a perimeter sidewall extending between the superior base surface and the inferior base surface, (ii) the perimeter sidewall has a number of pockets formed therein, and (iii) each of the pockets formed in the perimeter sidewall has the porous-metal coating disposed therein.

2. The orthopaedic implant of claim 1, wherein the polymer bearing is molded into the pockets of the solid-metal base.

3. The orthopaedic implant of claim 1, wherein:
a superior end of each of the pockets is defined by an opening formed in the superior base surface,
an inferior end of each of the pockets is defined by a base wall that is spaced apart inferiorly from the opening, and
two sides of the pockets are defined by a pair of sidewalls that extend from the opening to the base wall, with the sidewalls having the undercuts formed therein.

4. The orthopaedic implant of claim 3, wherein the surfaces of the sidewalls defining the undercut comprise rounded surfaces.

5. The orthopaedic implant of claim 1, wherein the number of pockets includes a number of adjacent pockets that open into one another.

6. The orthopaedic implant of claim 1, wherein: the tibial component further comprises a polymer stem extending away from the inferior base surface of the solid-metal base.

7. The orthopaedic implant of claim 6, wherein:
the solid-metal base has a central opening defined therein, and
the polymer bearing and the polymer stem define a monolithic structure that extends through the central opening.

8. The orthopaedic implant of claim 1, wherein each of the pockets has the porous-metal coating disposed therein.

9. An orthopaedic implant, comprising:
a polymer tibial bearing having (i) a bearing surface configured to articulate with a pair of femoral condyles of a femoral component, and (ii) an inner sidewall that defines an opening therein, and
a tibial component configured to be implanted on a surgically-prepared proximal end of a patient's tibia, the tibial component comprising:
a solid-metal base comprising (i) a superior base surface having a number of pockets formed therein with each of the pockets having an undercut formed therein, and (ii) an inferior base surface having a number of pegs extending outwardly therefrom,
a porous-metal coating disposed on the inferior base surface and the pegs, and
a polymer locking plate molded to the superior base surface of the solid-metal base, the polymer locking plate having a generally Y-shaped posterior buttress extending upwardly from a superior surface of the polymer locking plate, the posterior buttress being configured to be received in the opening of the tibial bearing to prevent rotation of the tibial bearing relative to the tibial component, wherein (i) the solid-metal base further comprises a perimeter sidewall extending between the superior base surface and the inferior base surface, (ii) the perimeter sidewall has a number of pockets formed therein, and (iii) each of the pockets formed in the perimeter sidewall has the porous-metal coating disposed therein.

10. The orthopaedic implant of claim 9, wherein the polymer bearing is molded into the pockets of the solid-metal base.

11. The orthopaedic implant of claim 9, wherein:

a superior end of each of the pockets is defined by an opening formed in the superior base surface, an inferior end of each of the pockets is defined by a base wall that is spaced apart inferiorly from the opening, and two sides of the pockets are defined by a pair of sidewalls that extend from the opening to the base wall, with the sidewalls having the undercuts formed therein.

12. The orthopaedic implant of claim 11, wherein the surfaces of the sidewalls defining the undercut comprise rounded surfaces.

13. The orthopaedic implant of claim 9, wherein the number of pockets includes a number of adjacent pockets that open into one another.

14. The orthopaedic implant of claim 9, wherein: the tibial component further comprises a polymer stem extending away from the inferior base surface of the solid-metal base.

15. The orthopaedic implant of claim 14, wherein:

the solid-metal base has a central opening defined therein, and the polymer locking plate and the polymer stem define a monolithic structure that extends through the central opening.

16. The orthopaedic implant of claim 9, wherein each of the pockets has the porous-metal coating disposed therein.

* * * * *